United States Patent [19]

Galantay

[11] 3,969,415

[45] July 13, 1976

[54] 1-(2-NAPHTHYL)-2,3-BUTADIEN-1-OLS

[75] Inventor: Eugene E. Galantay, Liestal, Switzerland

[73] Assignee: Sandoz, Inc., E. Hanover, N.J.

[22] Filed: Oct. 1, 1973

[21] Appl. No.: 402,468

Related U.S. Application Data

[63] Continuation-in-part of Ser. No. 203,825, Dec. 1, 1971, abandoned.

[52] U.S. Cl. ............ 260/613 D; 260/239 B; 260/247; 260/247.1 R; 260/293.62; 260/326.5 C; 260/326.5 S; 260/345.9; 260/347.2; 260/347.8; 260/456 R; 260/456 P; 260/501.15; 260/567.6 M; 260/570.5 R; 260/570.5 CA; 260/570.5 S; 260/609 F; 260/618 D; 260/618 E; 260/618 F; 424/337; 424/341; 424/343

[51] Int. Cl.² .............. C07C 43/20; C07C 33/06; C07C 149/00

[58] Field of Search......... 260/613 D, 618 B, 618 F, 260/612 D, 611 F, 618 R, 609 F, 618 D

[56] References Cited

UNITED STATES PATENTS

| | | | |
|---|---|---|---|
| 3,562,336 | 2/1971 | Nelson | 260/613 D |
| 3,626,012 | 12/1971 | Fried et al. | 260/599 |
| 3,641,161 | 2/1972 | Fried et al. | 260/613 D |
| 3,651,148 | 3/1972 | Nelson | 260/613 D |

OTHER PUBLICATIONS

Cherkasov et al., Chem. Abstract, 66, 7576 on, (1967).

Petrov et al., Chem. Abstract, 54, 8677h.

Primary Examiner—James O. Thomas, Jr.
Assistant Examiner—Nicky Chan
Attorney, Agent, or Firm—Gerald D. Sharkin; Richard E. Vila; Frederick H. Weinfeldt

[57] ABSTRACT

Disclosed are compounds of the class 1-naphthyl-2,3-butadien-1-ol e.g. 2-(6'-methoxy-2-naphthyl)-3,4-pentadien-2-ol, which are useful by reason of their pharmacological activity in animals, e.g. as anti-inflammatory agents. Said compounds can be readily prepared by reduction of a corresponding 4-substituted-1-naphthyl-2-butyne-1-ol with a complex hydride such as lithium aluminium hydride.

14 Claims, No Drawings

1-(2-NAPHTHYL)-2,3-BUTADIEN-1-OLS

This is a continuation-in-part of copending application, Ser. No. 203,825, filed Dec. 1, 1971 (now abandoned).

The invention relates to 1-naphthyl-2,3-butadien-1-ols and to pharmaceutical compositions and methods utilizing the pharmacological activity of said compounds.

The compounds of the present invention can be represented by the formula I

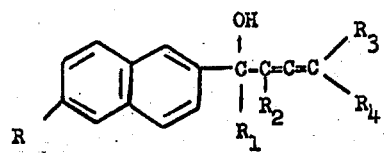

wherein
R is hydrogen, fluoro, chloro, bromo, alkyl of 1 to 4 carbon atoms, e.g. methyl, ethyl alkoxy of 1 to 4 carbon atoms, e.g. methoxy, propoxy, alkylthio of 1 to 4 carbon atoms, e.g. methylthio, or difluoromethoxy.

$R_1$ is hydrogen or alkyl of 1 to 3 carbon atoms, e.g. methyl, $R_2$ is hydrogen or methyl, and $R_3$ and $R_4$ are, independently, hydrogen or alkyl of 1 to 3 carbon atoms provided that at least one of $R_3$ and $R_4$ is hydrogen when $R_2$ is methyl.

The compounds of formula I in which $R_2$ is hydrogen, i.e. the compounds of formula Ia

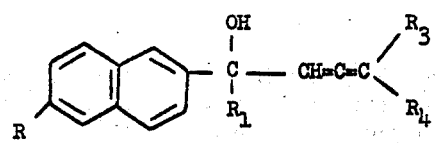

wherein R, $R_1$, $R_3$ and $R_4$ are as defined above, can be prepared by subjecting a compound of formula II

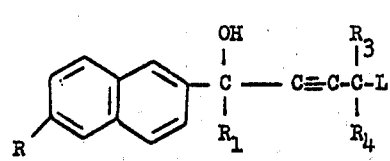

wherein
R, $R_1$, $R_3$ and $R_4$ are as defined above and
L is

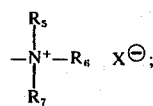

tetrahydrofuran-2-yloxy; tetrahydropyran-2-yloxy or 4-methoxy-tetrahydropyran-4-yloxy; halo, e.g., fluoro, chloro, bromo or iodo; alkylsulfonyloxy in which the alkyl group may be substituted, e.g. halo, or unsubstituted and contain from 1 to as many as 16 or more, preferably 1 to 6, carbon atoms, e.g. methane sulfonyloxy, ethanesulfonyloxy, 3-chloropropanesulfonyloxy, 1-hexadecanesulfonyloxy; or arylsulfonyloxy in which the aryl group is phenyl, naphthyl or mono or polysubstituted phenyl in which the substituents are, e.g. alkyl of 1 to 6 carbon atoms, alkoxy of 1 to 6 carbon atoms, halo, or nitro;

$R_7$ represents alkyl having 1 to 4 carbon atoms, e.g. methyl, ethyl, propyl or butyl including isomeric forms where they exist, although the unbranched alkyls are preferred, especially methyl, and $R_5$ and $R_6$ independently represent alkyl having 1 to 4 carbon atoms; cycloalkyl having 5 or 6 ring carbon, i.e. cyclopentyl or cyclohexyl; or together, with N, represents a heterocyclic ring having 5 to 7 members selected from the group consisting of pyrrolidino, piperidino, homopiperidino, morpholino, thiomorpholino, and their alkyl substituted derivatives containing 1 to 3 alkyl groups of 1 to 4 carbon atoms;

X is an anion derived from a mineral acid or an organic sulfonic acid, provided that X is not fluoro, to the action of a complex hydride reducing agent of the formula IIIa or IIIb:

wherein
T is a "tervalent" transition metal or non-metal such as aluminum, gallium or boron, i.e. an element of Group IIIa of the periodic table having atomic weight of from 10 to 70; and $Z^1$, $Z^2$ and $Z^3$ are, independently, a hydrogen atom, alkyl of 1 to 6 carbon atoms, alkoxy of 1 to 6 carbon atoms; or alkoxyalkoxy having from 2 to 6 carbon atoms in the alkylene portion thereof and from 1 to 6 carbon atoms in the alkoxy portion thereof;

$Z^4$ and $Z^5$ are, independently, hydrogen or alkyl of 1 to 6 carbon atoms; and M is an alkali or alkaline earth metal, such as lithium, sodium, potassium, calcium or magnesium, such as lithium hydride, sodium dihydrobis (2-methoxyethoxy) aluminate, sodium diethyl aluminum dihydride, lithium borohydride, lithium gallium hydride, magnesium aluminum hydride, lithium diisobutylmethyl aluminum hydride, lithium trimethoxy aluminum hydride, diethyl aluminum hydride and diborane, preferably lithium aluminum hydride or sodium dihydrobis (2-methoxyethoxy) aluminate.

The compounds of formula I in which $R_2$ is methyl, i.e. the compounds of formula Ib

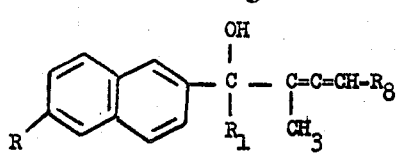 Ib

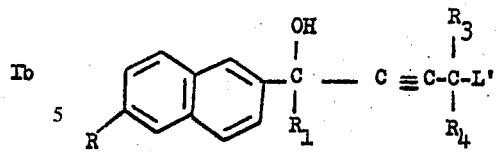 IIa wherein
R and $R_1$ are as defined above, and
$R_8$ is the same as either $R_3$ or $R_4$ defined above,
can be prepared by treating a compound of the formula IV

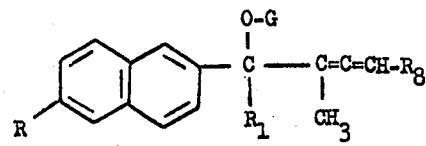 IV wherein
R, $R_1$, $R_8$ are as defined above, and
G is a protecting group stable under basic conditions, e.g. tetrahydropyran-2-yl tetrahydrofuran-2-yl and the like
with a mild acid, e.g. paratoluene sulfonic acid.

The process for preparing the compounds of formula Ia should be carried out in a medium which is not detrimental to the reaction, such as in an aprotic organic solvent, e.g. an ether such as diethyl ether, tetrahydrofuran or dioxane, an aromatic medium, such as benzene, toluene or pyridine or a saturated aliphatic hydrocarbon, such as pentane, hexane or octane. The use of a solvent which is capable of dissolving the compound II, at the reaction temperature is preferred. The medium may be a mixture or a single material. The reaction, e.g. may be carried out at from about −40° to +120°C., e.g. at the boiling point of the medium. However, temperatures of from about −10° to +50°C. are preferred. While the higher temperatures result in a faster reaction rate, reactions carried out at lower temperature tend to give purer products. The reaction product (compound Ia) may be recovered by conventional means, e.g. by carefully adding a small amount of water or aqueous sodium sulfate to the reaction mixture, filtering off the inorganic by-products or hydrolysis products of the hydride ion source, and then separating the Compound Ia from the organic phase by such means as precipitation, extraction, crystallization, chromatography or liquid-liquid extraction. As will be appreciated by those skilled in the art, it is preferred to exclude moisture from the reaction, e.g. by use of anhydrous solvents and conditions. The reaction may be advantageously carried out in an inert atmosphere, e.g. under nitrogen gas.

The process for producing compounds of formula Ib, which comprises the splitting off of the protecting group G is effected under the acid condition usually employed for such a hydrolysis reaction, e.g. by using p-toluenesulfonic acid hydrate in methanol, ethanol or benzene. The protecting group G of compound IV is preferably a tetrahydropyranyl group.

The compounds of formula II in which L is a quaternary ammonium radical, i.e. the compounds of formula IIa wherein
R, $R_1$, $R_3$ and $R_4$ are as defined above and
L' is $$-\overset{R_5}{\underset{R_7}{N^+}}-R_6 \; X^-$$

in which $R_5$, $R_6$, $R_7$ and X are as defined above, can be prepared by quaternizing a compound of the formula V

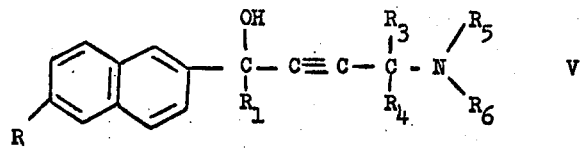 V wherein R, $R_1$, $R_3$, $R_4$, $R_5$ and $R_6$ are as defined above, with a compound of the formula VI $R_7X$        VI wherein $R_7$ and X are as defined above. The quaternization can be carried out in the conventional manner, e.g. in a suitable solvent such as acetone, at a temperature of from −20° to +30°C., neither the solvent nor the temperature being critical. A preferred compound VI is methyl iodide.

The compounds of formula II in which L is tetrahydrofuran-2-yloxy, tetrahydropyran-2-yloxy or 4-methoxy-tetrahydropyran-4-yloxy, i.e. the compounds of formula IIb

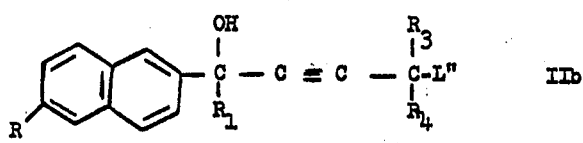 IIb wherein
R, $R_1$, $R_3$ and $R_4$ are as defined above and
L'' is tetrahydrofuran-2-yloxy, tetrahydropyran-2-yloxy or 4-methoxy-tetrahydropyran-4-yloxy
can be prepared by reacting a compound of the formula VII

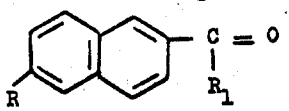 VII wherein R and R₁ are as defined above, with Grignard reagent formed by treating a compound of the formula VIII

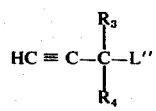 VIII wherein R₃, R₄ and L″ are as defined above, with ethyl magnesium bromide.

The compounds of formula II in which L is halo other than iodo, i.e., those compounds of formula IIc

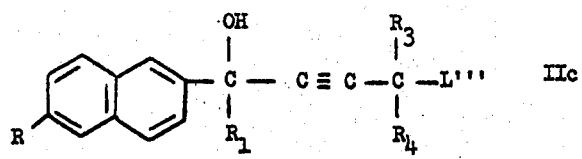 IIc wherein

R, R₁, R₃ and R₄ are as defined above and
L‴ is fluoro, chloro or bromo can be prepared by reacting a compound of the formula IX

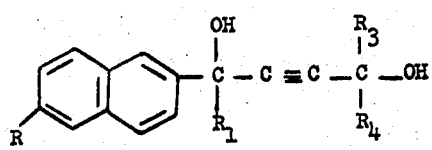 IX wherein R, R₁, R₃ and R₄ are as defined above with the appropriate halide selected from the group of thionyl chloride or bromide, phosphorus pentachloride or bromide and hydrocarbon sulfonyl fluorides, e.g. benzyl sulfonyl fluoride, tosyl fluoride and mesyl fluoride in an organic medium such as hexane, benzene or dimethoxyglycol. For the chlorination and bromination a tertiary amine base, such as pyridine, is included in the reaction mixture and the reaction temperature is about 0° to 20°C. For the fluorination the reaction temperature is 0° to about 150°C.

Compounds of formula II in which L is iodo are conveniently prepared by reacting corresponding compounds of formula IIc in which L‴ is chloro, with sodium iodide in acetone, the reaction being carried out in conventional manner.

The compounds of formula II in which L is alkylsulfonyloxy or arylsulfonyloxy, i.e. the compounds of formula IId

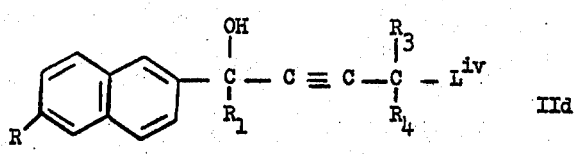 IId wherein

R, R₁, R₃ and R₄ are as defined above and
$L^{iv}$ is alkylsulfonyloxy or arylsulfonyloxy as defined above can be prepared by reacting a compound of the formula IX above with an appropriate alkylsulfonyl chloride, such as methanesulfonyl chloride, 3-chloropropanesulfonyl chloride or 1-hexadecanesulfonyl chloride or arylsulfonyl chloride, such as benzenesulfonyl chloride, 4-toluenesulfonyl chloride or 2-naphthalenesulfonyl chloride. This reaction is conveniently carried out in pyridine at or about room temperature.

The compounds of formula IIIa and IIIb used in the reduction of compounds II are known.

The compounds of formula IV used in the preparation of compounds Ib can be produced by isomerizing a compound of the formula X

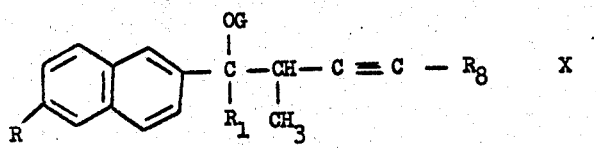 X wherein R, R₁, R₈ and G are as defined above with a strong base, e.g. sodium hydroxide or potassium hydroxide in a suitable solvent, such as ethanol, butanol, dimethyl acetamide or, preferably, dimethyl sulphoxide. The isomerization is carried out at a temperature of up to 160°C., preferably 50°C. to 90°C., and preferably in the absence of water.

The compounds of formula V above can be prepared by reacting a compound of formula VII above with a compound of formula XI

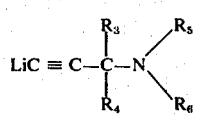 XI wherein $R_3$, $R_4$, $R_5$ and $R_6$ are as defined above. This reaction can be carried out at temperatures of 0° to 50°C., conveniently at room temperature, and in the presence of an organic solvent such as tetrahydrofuran.

The compounds of formula V can also be prepared by a process which involves reacting a compound of formula XII

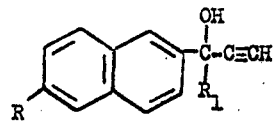  XII wherein R and $R_1$ are as defined above, with a product formed by condensing a compound of formula XIII

  XIII wherein $R_3$ and $R_4$ are as defined above, with a compound of formula XIV

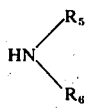  XIV wherein $R_5$ and $R_6$ are as defined above, said condensation product preferably prepared under conditions whereby water is eliminated when either of $R_3$ and $R_4$ is other than hydrogen.

The condensation of compounds XIII and XIV is preferably carried out separately at temperatures of from 10° to 130°C., and when either of $R_3$ and $R_4$ is alkyl, it is preferably carried out at the higher temperature, e.g. reflux in the presence of an acid catalyst such as paratoluene sulfonic acid and a solvent such as benzene which is capable of forming an azeotrope with the water formed. The condensation product is reacted with the compound of formula XII at a temperature of 50° to 150°C. in the presence of an inert solvent, and preferably in the presence of mono-valent copper ion, as catalyst, preferably cuprous chloride or cuprous oxide, although salts and the like of other coinage metals, i.e., silver and gold (I), can be used.

The compounds of formula VI above are known per se or can be prepared from known materials by conventional methods.

The compounds of formula VII used in the production of compounds IIb are known or can be prepared from known compounds using conventional techniques.

The compounds of formula VIII are prepared by reacting a propargyl alcohol with dihydrofuran, dihydropyran or 4-methoxy-5,6-dihydro-2H-pyran in the presence of hydrochloric acid, phosphorus oxychloride or other condensation agent.

The compounds of formula IX used in the production of compound IIc and IId can be prepared by conventional hydrolysis of a compound of formula IIb, such as with a mineral or organic acid.

The compounds of formula X above are prepared by reacting a compound of formula XV

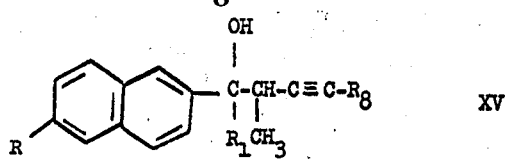  XV wherein R, $R_1$, and $R_8$ are as defined above, with dihydrofuran or dihydropyran in a manner similar to that described above for the preparation of compounds of formula VIII.

The compounds of formula XI are known or can be produced in known manner by reacting a compound of the formula XVI

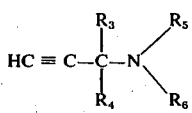  XVI wherein $R_3$, $R_4$, $R_5$ and $R_6$ are as defined above with lithium at a temperature of 0° to 50°C. in a suitable solvent such as ethylene diamine.

The compounds of formula XII can be prepared by reacting a compound of formula VII above in a solvent such as dimethyl acetamide with a suitable acetylene reagent, such as sodium or lithium acetylide conveniently at room temperature.

The compounds of formulae XIII and XIV used in the preparation of compound V are known or can be produced from known materials by conventional techniques.

The compounds of formula XV can be prepared by reacting a compound of formula VII with a suitable organo-metallo reagent XVII

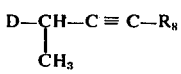  XVII wherein
  $R_8$ is as defined above, and
  D is an equivalent unit of either an active metal or a polyvalent active metal halide, e.g., an alkali metal, such as lithium, potassium or sodium, aluminum, zinc, or magnesium bromide or iodide
to obtain the D salt of the resulting compound XV, which on hydrolysis yields the desired compound XV. The procedure may be carried out under conditions conveniently employed in carrying out "Grignard-type" reactions, e.g., in an aprotic organic medium at a temperature of from about −30° to 100°C., preferably from about −20°C. to 50°C., followed by standard hydrolysis of the resulting D salt in an aqueous medium, e.g. water or a highly concentrated aqueous salt solution, e.g., saturated ammonium chloride solution. The medium used is dependent upon the composition of the organo-metallo reagent. For example, if D is MgBr, MgI or Li, the medium may be ether or tetrahydrofuran, if D is Na, the medium may be liquid ammonia-ether, liquid ammonia-tetrahydrofuran, dioxane, pyridine or dioxane-pyridine. The temperature and medium are not critical.

The compounds of formula XVI and XVII are known or can be produced in known manner from available materials.

Compounds Ib may also be obtained by an alternative process (process b') which involves treating a Compound VII with a Grignard reagent prepared from a compound of formula XX.

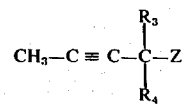

XX in which $R^3$ and $R^4$ are as defined above, and Z is bromo, chloro or iodo, and hydrolyzing the resulting product, i.e., the corresponding "Grignard salt" of the resultant Compound Ib.

In process (b'), the reaction of the Grignard reagent with the compound of formula VII and the subsequent hydrolysis may be carried out in conventional manner. Preferred solvents for the reaction include diethyl ether, tetrahydrofuran, dioxane, benzene and toluene. Preferred temperatures for the reaction are from −10°C to +90°C, more preferably from +25° to +65°C. It is preferred to exclude moisture from the reaction. The reaction is advantageously carried out under an inert atmosphere, e.g., of nitrogen or argon. The hydrolysis may conveniently be effected by careful addition to the reaction mixture of water, aqueous sodium sulphate solution, aqueous ammonium chloride solution or dilute acid. The Grignard reagent may be produced in the conventional manner. The resulting compound Ib likewise may be isolated in conventional manner.

The compounds of formula I are useful because they possess pharmacological activity in animals. In particular, the compounds I are useful as anti-inflammatory agents as indicated by the Carrageenan induced edema test on rats (oral administration at 1 to 200 mg/kg). For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1 milligram to about 250 milligrams per kilogram, e.g., from about 1 milligram to about 175 milligrams per kilogram, of body weight, preferably given in divided doses 2 to 4 times a day, or in sustained release form. For most mammals, the administration of from about 60 milligrams to about 3000 milligrams, e.g., from about 160 milligrams to about 2000 milligrams, of the compound per day provides satisfactory results and dosage form suitable for internal administration comprise from about 15 milligrams to about 1500 milligrams, e.g., from about 40 milligrams to about 1000 milligrams, of the compound in admixture with a solid or liquid pharmaceutical carrier or diluent.

For the above usage, oral administration with carriers may take place in such conventional forms as tablets, dispersible powders, granules, capsules, syrups and elixirs. Such compositions may be prepared according to any method known in the art for manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert solid diluent, e.g. calcium carbonate, calcium phosphate and kaolin. The preferred pharmaceutical compositions from the standpoint of preparation and ease of administration are solid compositions, particularly tablets and solid or liquid diluent-filled capsules.

A particularly valuable compound of this invention is 2-(6'-methoxy-2'-naphthyl)-3,4-pentadien-2-ol.

Representative formulations of a tablet and a capsule prepared by conventional techniques are as follows:

| Ingredient | Weight | |
| --- | --- | --- |
| | Tablet | Capsule |
| 1-naphthyl-2,3-butadien-1-ol or 2-(6'-methoxy-2'-naphthyl)-3,4 pentadien-2-ol | 50 | 50 |
| Tragacanth | 10 | |
| Lactose | 197.5 | 250 |
| Corn Starch | 25 | |
| Talcum | 15 | |
| Magnesium Stearate | 2.5 | |

In the following examples which are illustrative of the invention, temperatures are in degrees centrigrade, and room temperature is 20° to 30°C., unless indicated otherwise.

EXAMPLE 1

2-(6'-Methoxy-2'-naphthyl)-3,4-pentadien-2-ol

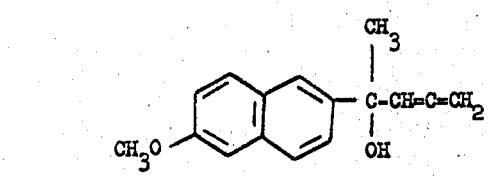

Step A 84 g. of lithium wire is dissolved in 2200 ml. of ethylene diamine. Then, at 0°C. 1040 g. of 3-dimethylamino-1-propyne is added dropwise. Finally a solution of 70.0 g. of 6-methoxy-2-acetonaphthone in 500 ml. of anhydrous tetrahydrofuran is added, and the mixture is stirred at 25°C. for 18 hours. The mixture is poured onto ice and the product of this step, 2-(6'-methoxy-2'-naphthyl)-5-dimethylamino-3-pentyn-2-ol, is obtained by extraction with methylene chloride.

Step B

The product of step A is dissolved in 1 liter of acetone, and at 0°C. is treated with 60 ml. of methyl iodide. After 18 hours at 5°C. the mixture is evaporated and the residue is treated with 500 ml. of ether. The product of this step, 2-(6'-methoxy-2'-naphthyl)-5-dimethylamino-3-pentyn-2-ol methiodide is obtained by filtration and washing with ether, m.p. 114°–7°C.

Step C 102 g. of the product of Step B, 2000 ml. of anhydrous tetrahydrofuran and 17.4 g. of lithium aluminum hydride is stirred at room temperature for 18 hours, then treated with 26 ml. of 15% aqueous NaOH followed by solid sodium sulfate, and filtered. The filtrate is evaporated to dryness, taken up in ether, washed and dried. The ether solution upon standing at 5° yields crystals of 2-(6'-methoxy-2'-naphthyl)-3,4-pentadien-2-ol, m.p. 46°–50°C.

EXAMPLE 2

Repeating the procedure of Example 1, but using in place of the 6-methoxy-2-acetonaphthone use therein, an approximately equivalent amount of:
 a. 6-methoxy-2-naphthaldehyde,
 b. 6-methoxy-2-proprionaphthone,
 c. 6-methoxy-2-isobutyronaphtone,
 d. 6-chloro-2-acetonaphthone, or
 e. 2-acetonaphthone;
there is accordingly obtained the amino intermediate:
 a. 4-dimethylamino-1-(6'-methoxy-2'-naphthyl)-2-butyn-1-ol,
 b. 1-dimethylamino-4-(6'-methoxy-2'-naphthyl)-2-hexyn-4-ol,
 c. 1-dimethylamino-4-(6'-methoxy-2'-naphthyl)-5-methyl-2-hexyn-4-ol,
 2-(6'-chloro-2'-naphthyl)-5-dimethylamino-3-pentyn-2-ol, or
 e. 5-dimethylamino-2-(2'-naphthyl)-3-pentyn-2-ol;
from which in turn via the respective methyl iodide salt thereof, is obtained:
 a. 1-(6'-methoxy-2'-naphthyl)2,3-butadien-1-ol, m.p. 73°–75°,
 b. 3-(6'-methoxy-2'-naphthyl)-4,5-hexadien-3-ol, refractive index 1.673 at 23°, or
 c. 3-(6'-methoxy-2'-naphthyl)-2-methyl-4,5-hexadien-3-ol, refractive index 1.6076 at 23°,
 d. 2-(6'-chloro-2'-naphthyl)-3,4-pentadien-2-ol, m.p. 60°–61°, or
 e. 2-(2'-naphthyl)-3,4-pentadien-2-ol, m.p. 48°.

EXAMPLE 3

Repeating the procedure of Example 1, but replacing the 6-methoxy-2-acetonaphthone used therein with an approximately equivalent amount of 6-chloro-2-acetonaphthone, and replacing the 3-dimethylamino-1-propyne used there with an approximately equivalent amount of 3-dimethylamino-3-methyl-1-butyne, there is obtained the intermediate 2-(6'-chloro-2'-naphthyl)-5-dimethylamino-5-methyl-3-hexyn-2-ol, from which in turn via the methyl iodide salt thereof is obtained 2-(6'-chloro-2'-naphthyl)-5-methyl-3,4-hexadien-2-ol, b.p. 130°–150° at 0.4 mm.

EXAMPLE 4

Repeating the procedure of Example 3 but replacing the 6-chloro-2-acetonaphthone used therein with an approximately equivalent amount of:
 a. 2-acetonaphthone
 b. 6-methoxy-2-propionaphthone, or
 c. 6-methoxy-2-isobutyronaphthone;
there is accordingly obtained the amino intermediate:
 a. 5-dimethylamino-5-methyl-2-(2'-naphthyl)-3-hexyn-2-ol,
 b. 6-dimethylamino-3-(6'-methoxy-2'-naphthyl)-6-methyl-4-heptyn-3-ol, or
 c. 2,6-dimethyl-6-dimethylamino-3-(6'-methoxy-2'-naphthyl)-4-heptyn-3-ol;
from which in turn via the respective methyl iodide salt thereof, is obtained respectively:
 a. 2-(2'-naphthyl)-5-methyl-3,4-hexadien-2-ol as a liquid,
 b. 3-(6'-methoxy-2'-naphthyl)-6-methyl-4,5-heptadien-3-ol, m.p. <40°, or
 c. 3-(6'-methoxy-2'-naphthyl)-2,6-dimethyl-4,5-heptadien-3-ol, m.p. 105°.

EXAMPLE 5

Repeating the procedure of Example 1, but using in place of the 6-methoxy-2-acetonaphthone used therein, an approximately equivalent amount of 2-acetonaphthone, and in place of the dimethylaminopropyne used therein, an approximately equivalent amount of 3-dimethylamino-1-pentyne, there is accordingly obtained the amino intermediate, 5-dimethylamino-2-(2'-naphthyl)-3-heptyn-2-ol, which via the methyl iodide salt thereof yields 2-(2'-naphthyl)-3,4-heptadien-2-ol as a liquid.

EXAMPLE 6

1-(6'-Methoxy-2'-naphthyl)-2,3-butadien-1-ol

Step A

To a Grignard mixture prepared in the conventional manner from 6.1 g. of magnesium (etched with iodine) and 27.2 g. of ethyl bromide in a total of 120 ml. of dry tetrahydrofuran, there is dropwise added a solution of 32.2 g. of 3-(2'-tetrahydropyranyloxy)-propyne in 32 ml. of dry tetrahydrofuran. After 1 hour stirring at room temperature, a solution of 36.6 g. of 6-methoxy-2-naphthaldehyde in 200 ml. of dry tetrahydrofuran is dropwise added. After 1 hour stirring at room temperature, the reaction is poured onto saturated ammonium chloride solution. The aqueous phase is extracted once with benzene. The combined organic solutions are washed with 500 ml. of 1N potassium hydroxide and then with 300 ml. of water, dried over sodium sulfate and evaporated to dryness to obtain 1-(6'-methoxy-2'-naphthyl)-4-(tetrahydropyran-2-yloxy)-2-butyn-1-ol.

Step B

To a solution of 57.0 g. of the product from step A in 350 ml. of dry tetrahydrofuran there is added dropwise 110 ml. of lithium aluminum hydride in ether (0.90 molar) at approximately 10°C. After 24 hours stirring at room temperature, the reaction mixture is cooled in an ice bath and there is slowly added, 10 ml. of 20% aqueous potassium hydroxide, followed by the addition of 10 g. of sodium sulfate. The filtered solution is evaporated to obtain crude product which is then subjected to chromatographic separation to obtain 1-(6'-methoxy-2'-naphthyl)-2,3-butadien-1-ol.

EXAMPLE 7

2-(2'-Naphthyl)-3,4-heptadien-2-ol

Step A

To a solution of 50 g. of 2'-acetonaphthone in 250 ml. of dimethylsulfoxide, is added 82 g. of lithium acetylide portionwise at room temperature under nitrogen over a period of 30 minutes. The mixture is stirred overnight at room temperature under nitrogen. The reaction mixture is then poured onto ice, extracted with chloroform, the chloroform solution washed twice with water, dried over sodium sulfate and evaporated to dryness. Distillation at reduce pressure provides 2-(2'-naphthyl)-3-butyn-2-ol.

Step B 52 g. of the product from step A is dissolved in 260 ml. of dioxane, then heated to 60°C., then 1.0 g. of cuprous chloride is added, followed by a dropwise addition of 31 g. of n-propenyl piperidine in 155 ml. of dioxane over a period of 10 minutes. When reaction is complete,* cooled and most of the dioxane evaporated off. The mixture is then quenched with water and extracted with ether. The ether solution is washed twice with water, dried over sodium sulfate and evaporated to dryness to obtain crude 2-(2'-naphthyl-5-(1'-piperidinyl)-3-heptyn-2-ol.

* As indicated by thin layer chromatography, i.e., from 1 to 2 hours.

Step C 75 g. of the product from step B is dissolved in 525 ml. of acetonitrile, cooled in an ice bath, and to it added a solution of 10 g. methyl iodide in 35 ml. of ether in an apparatus free of moisture. The mixture is stirred overnight in cold room, solvent stripped off, the crude product dissolved in a minimum amount of acetone and finally ether added to precipitate out the product, 2-(2'-naphthyl)-5-(1'-piperidinyl)-3-heptyn-2-ol methiodide.

Step D

To suspension of 18 g. of product from step C in 180 ml. of absolute tetrahydrofuran, is added 15 ml. of 35% (W/W) solution of sodium dihydro bis-(methoxyethoxy)aluminate in benzene at room temperature under nitrogen dropwise. The reaction mixture is stirred at room temperature until reaction is complete then there is added slowly, 40 ml. of one normal sodium hydroxide solution, then filtered through celite and then concentrated by evaporating off most of the tetrahydrofuran. Benzene is added, the benzene solution is washed with water, dried over sodium sulfate, stripped and then distilled to obtain the product 2-(2'-naphthyl)-3,4-heptadien-2-ol.

EXAMPLE 8

Repeating the procedure of Example 6, but replacing the Grignard mixture prepared from 3-(2'-tetrahydropyranyloxy)-propyne used therein, with a Grignard mixture prepared from an approximately equivalent amount of 3-methyl-3-(2'-tetrahyropyranyloxy)-1-butyne, and replacing the 6-methoxy-2-naphthaldehyde, used therein with an approximately equivalent amount of:
 a. 2-acetonaphthone
 b. 6-methoxy-2-propionaphthone,
 c. 6-methoxy-2-isobutyronaphthone, or
 d. 6-chloro-2-acetonaphthone;
there is accordingly obtained the intermediate (IIb):
 a. 5-(2'-tetrahydropyranyloxy)-5-methyl-2-(2'-naphthyl)-3-hexyn-2-ol,
 b. 6-(2'-tetrahydropyranyloxy)3-(6'-methoxy-2'-naphthyl)-6-methyl-4-heptyn-3-ol,
 c. 2,6-dimethyl-6-(2'-tetrahydropyranyloxy)-3-(6'-methoxy-2'-naphthyl)-4-heptyn-3-ol, or
 d. 2-(6'-chloro-2'-naphthyl)-5-(2'-tetradropyranyloxy)5-methyl-3-hexyn-2-ol;

from which by treatment with lithium aluminum hydride (a and d) or an equivalent amount of sodium dihydrobis (2-methoxyethoxy) aluminate (b and c) there is obtained respectively:
 a. 2-(2'-naphthyl-5-methyl-3,4-hexadien-2-ol,
 b. 3-(6'-methoxy-2'-naphthyl)-6-methyl-4,5-heptadien-3-ol,
 c. 3-(6'-methoxy-2'-naphthyl)-2,6-dimethyl-4,5-heptadien-3-ol, or
 d. 2-(6'-chloro-2'-naphthyl)-5-methyl-3,4-hexadien-2-ol.

What is claimed is:

1. A compound of the formula

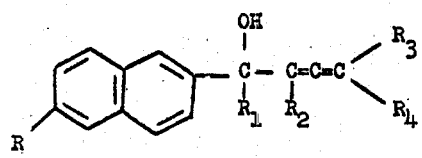

wherein
R is hydrogen, fluoro, chloro, bromo, alkyl of 1 to 4 carbon atoms, alkoxy of 1 to 4 carbon atoms, alkylthio of 1 to 4 carbon atoms or difluoromethoxy;
$R_1$ is hydrogen or alkyl of 1 to 3 carbon atoms;
$R_2$ is hydrogen or methyl; and
$R_3$ and $R_4$ are, independently, hydrogen or alkyl of 1 to 3 carbon atoms provided that at least one of $R_3$ and $R_4$ is hydrogen when $R_2$ is methyl.

2. A compound of claim 1 wherein $R_2$ is methyl.
3. A compound of claim 1 wherein $R_2$ is hydrogen.
4. The compound of claim 3 which is 2-(6'-methoxy-2'-naphthyl)-3,4-pentadien-2-ol.
5. The compound of claim 3 which is 2-(6'-chloro-2'-naphthyl)-3,4-pentadien-2-ol.
6. The compound of claim 3 which is 1-(6'-methoxy-2'-naphthyl)-2,3-butadien-1-ol.
7. The compound of claim 3 which is 2-(2'-naphthyl)-5-methyl-3,4-hexadien-2-ol.
8. The compound of claim 3 which is 2-(2'-naphthyl)-3,4-heptadien-2-ol.
9. The compound of claim 3 which is 2-(2'-naphthyl)-3,4-pentadien-2-ol.
10. The compound of claim 3 which is 3-(6'-methoxy-2'-naphthyl)-6-methyl-4,5-heptadien-3-ol.
11. The compound of claim 3 which is 3-(6'-methoxy-2'-naphthyl)-2,6-dimethyl-4,5-heptadien-3-ol.
12. The compound of claim 3 which is 3-(6'-methoxy-2'-naphthyl)-2-methyl-4,5-hexadien-3-ol.
13. The compound of claim 3 which is 3-(6'-methoxy-2'-naphthyl)-4,5-hexadien-3-ol.
14. The compound of claim 3 which is 2-(6'-chloro-2'-naphthyl)-5-methyl-3,4-hexadien-2-ol.

* * * * *